US008450360B2

(12) United States Patent
Himmler et al.

(10) Patent No.: US 8,450,360 B2
(45) Date of Patent: May 28, 2013

(54) PROCESS FOR PREPARING DITHIINE-TETRACARBOXIMIDES

(75) Inventors: Thomas Himmler, Odenthal (DE); Winfried Etzel, Leichlingen (DE); Frank Volz, Köln (DE)

(73) Assignee: Bayer CropScience AG, Monheim (DE)

( * ) Notice: Subject to any disclaimer, the term of this patent is extended or adjusted under 35 U.S.C. 154(b) by 85 days.

(21) Appl. No.: 13/086,512

(22) Filed: Apr. 14, 2011

(65) Prior Publication Data

US 2011/0269973 A1    Nov. 3, 2011

Related U.S. Application Data

(60) Provisional application No. 61/325,074, filed on Apr. 16, 2010.

(30) Foreign Application Priority Data

Apr. 14, 2010  (EP) .................................... 10159899

(51) Int. Cl.
*A61K 31/40*    (2006.01)
*C07D 491/00*   (2006.01)

(52) U.S. Cl.
USPC ......................................... 514/411; 548/431

(58) Field of Classification Search
USPC ......................................... 514/411; 548/431
See application file for complete search history.

(56) References Cited

U.S. PATENT DOCUMENTS

| 3,364,229 A | 1/1968 | Draber et al. |
| 2011/0257411 A1 | 10/2011 | Himmler |
| 2011/0275831 A1 | 11/2011 | Lui et al. |
| 2012/0022270 A1 | 1/2012 | Himmler et al. |

FOREIGN PATENT DOCUMENTS

| JP | 10-251265 A | 9/1998 |
| PL | 143 804 | 11/1988 |
| WO | WO 94/24985 A1 | 11/1994 |

OTHER PUBLICATIONS

Valla, et al, Synthetic Communications, vol. 36, 2006, pp. 3591-3597.*
Draber, W., "Synthese von 1.4-Dithiinen aus Derivaten des Maleinimids," *Chem. Ber.* 100:1559-1570, Deutsche Chemische Gesellschaft, Germany (1967).
Unverified English language translation of Draber, W., "Synthesis of 1,4-Dithiins from Maleimide Derivatives," *Chem. Ber* 100:1559-1570, Deutsche Chemische Gesellschaft, Germany (1967).
Unverified English language translation of Polish Patent Application No. 143 804, Patent Office of the Polish People's Republic, Poland, Date: Apr. 14, 2011.
Gülten, S., "The Synthesis and Characterization of Solvatochromic Maleimide-Fused N-Allyl- and N-Alkyl-Substituted 1,4-Dithiines and Diels-Alder Reactions with Anthracene," *J. Heterocyclic Chem.* 47:188-193, HeteroCorporation, United States (2010).
Katritzky, A.R. and Fan, W-Q., et al., "Some Novel Quinone-Type Dyes Containing Napthoquinone and Related Fused Ring Systems," *J. Heterocyclic Chem.* 25:901-906, Journal of Heterocyclic Chemistry, United States (1998).
Valla, A. et al., "Atypical Oxidation Reaction by Thionyl Chloride: Easy Two-Step Synthesis of N-Alkyl-1,4-dithiines," *Synthetic Communications* 36:3591-3597, Taylor & Francis Group, LLC, England (2006).
Yun, J.Y., et al., "Quantitative regio-selective Diels-Alder reaction of an unsymmetrical 1,4-dithiin and anthracene through heterogeneous solid state conversion," *Dyes and Pigments* 83:262-265, Elsevier Ltd., United States (2009).
Zentz, F., et al., "Syntheses, in vitro antibacterial and antifungal activities of a series of N-alkyl, 1,4-dithiines," *Il Farmaco* 60:944-947, Elsevier SAS, France (2005).
Database WPI/Thomson, Accession No. 1994-357851 [44], English language abstract, WO 94/24985, published Oct. 11, 1994.
English language abstract for Japanese Patent Application No. JP 10-251265 A, published Sep. 22, 1998, Japanese Patent Office, Espacenet database—Worldwide (1998).
International Search Report for International Application No. PCT/EP2011/055512, European Patent Office, Netherlands, mailed on May 26, 2011.

* cited by examiner

*Primary Examiner* — Susannah Chung
(74) *Attorney, Agent, or Firm* — Sterne, Kessler, Goldstein & Fox P.L.L.C.

(57) ABSTRACT

The present invention relates to a new process for preparing dithiine-tetracarboximides.

19 Claims, No Drawings

PROCESS FOR PREPARING DITHIINE-TETRACARBOXIMIDES

The present invention relates to a new process for preparing dithiine-tetracarboximides.

Dithiine-tetracarboximides as such are already known. It is also known that these dithiine-tetracarboximides can be used as anthelmintics against internal parasites of animals, more particularly nematodes, and have insecticidal activity (cf. U.S. Pat. No. 3,364,229). It is known, furthermore, that certain dithiine-tetracarboximides possess antibacterial activity and have a certain activity against causative organisms of human mycoses (cf. Il Farmaco 2005, 60, 944-947). It is also known that dithiine-tetracarboximides can be used as pigments in electrophotographic photoreceptors or as dyes in paints and polymers (cf. JP-A 10-251265, PL-B 143804).

Dithiine-tetracarboximides of the formula (I)

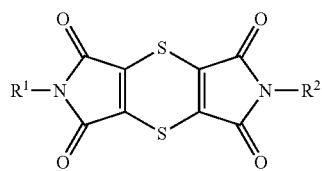

(I)

in which $R^1$ and $R^2$ are identical or different and are hydrogen, or are $C_1$-$C_8$-alkyl which is optionally substituted one or more times by halogen, —$OR^3$, and/or —$COR^4$, are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino, $R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl, $R^4$ is hydroxyl, $C_1$-$C_4$-alkyl or $C_1$-$C_4$-alkoxy, can be prepared in a variety of known ways.

For example, in one process (cf. U.S. Pat. No. 3,364,229; Chem. Ber. 1967, 100, 1559-1570), in a first stage, dichloromaleic anhydride of the formula (II) is reacted with an amine of the formula (III), optionally in the presence of a diluent. Subsequently, the resultant dichloromaleimides of the formula (IV) are then reacted with a sulphur compound (e.g. hydrogen sulphide or thiourea). The preparation of the dithiine-tetracarboximides of the formula (I) by this process can be illustrated by the following scheme:

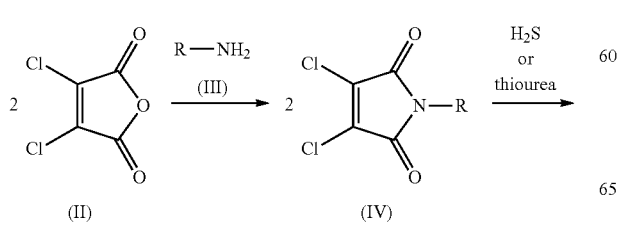

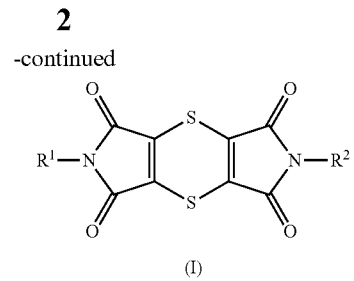

(I)

$R = R^1$ or $R^2$

This process has the disadvantage that, for example, operating with the highly toxic gaseous hydrogen sulphide is from a technical standpoint very difficult, costly and inconvenient. When thiourea is used, unwanted by-products are obtained along with the target product, and are very difficult to remove, and detract from the attainable yields (cf. J. Heterocycl. Chem. 1988, 25, 901-906).

In another process which has been disclosed (cf. Synthetic Communications 2006, 36, 3591-3597), in a first stage, succinic anhydride of the formula (V) is reacted with an amine of the formula (III), optionally in the presence of a diluent. Subsequently, the resultant succinic monoamides of the formula (VI) are reacted for 6 hours with a large excess of thionyl chloride in the presence of dioxane as diluent, at room temperature, to give, finally, in a sequence of numerous reaction steps, the dithiine-tetracarboximides of the formula (I). The dithiine-tetracarboximides are optionally isolated directly from the reaction mixture or by filtration following addition of water. Depending on reaction conditions (diluents) and the nature of the radicals R, it is possible in certain circumstances to isolate the dithiine-diisoimides of the formula (VII) before they are converted into the dithiine-tetracarboximides of the formula (I). This preparation method for the dithiine-tetracarboximides of the formula (I) can be illustrated by the following scheme:

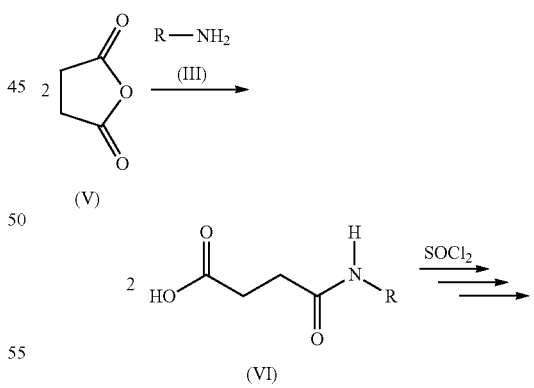

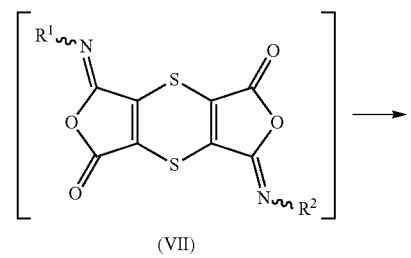

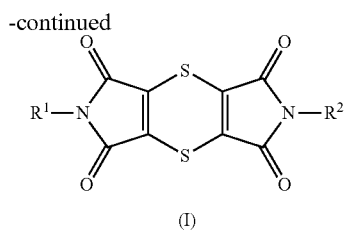

$R = R^1 \text{ or } R^2$

Disadvantages of this process are the long reaction time and also the outcome where either the yields obtained generally do not exceed about 30-40% of theory or else the purities of the isolated products are inadequate (see comparative examples). A further disadvantage, in the case of aqueous work-up of the reaction mixture, is that it involves destroying large amounts of thionyl chloride; the gases formed ($SO_2$ and HCl) have to be disposed of. Likewise a disadvantage is the fact that, from experience (see comparative examples), the product is not obtained in one fraction. Instead, it is frequently the case that, following initial isolation of product by filtration, further product precipitates from the filtrate after prolonged standing (overnight, for example), and must be isolated again by filtration. Occasionally this operation must be carried out once more. This procedure is very laborious and time-consuming.

It is known, moreover, that dithiine-tetracarboximides are obtained by dissolving N-substituted succinamides in dry 1,4-dioxane and then adding thionyl chloride to the solution. The reaction mixture is subsequently heated and the solution is concentrated in vacuo and, via column chromatography, is separated and purified (cf. J. Heterocycl. Chem. 2010, 47, 188-193).

Consequently there continues to be a need for a technically simple and economic preparation process for dithiine-tetracarboximides of the formula (I).

A new process has been found for preparing dithiine-tetracarboximides of the general formula (I)

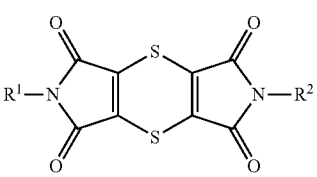

in which $R^1$ and $R^2$ have the definitions indicated above, characterized in that
in a first stage, succinic monoamides of the formula (VI)

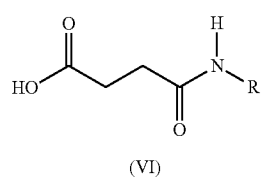

in which R is $R^1$ or $R^2$
are reacted with an excess of thionyl chloride, optionally in the presence of a diluent, then the excess of thionyl chloride is removed and the resulting product mixture is converted in a second stage, in an organic solvent, into the dithiine-tetracarboximides of the formula (I).

In this way the dithiine-tetracarboximides of the formula (I) can be obtained in relatively high yield, a relatively short time, and relatively good purity.

The product mixture obtained in the first step of the process of the invention also already includes dithiine-tetracarboximides of the formula (I), but its principal components are polysulphides of the formula (IX),

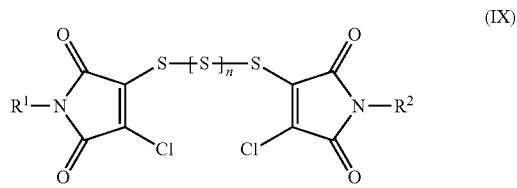

and also, depending on the work-up method, thiosulphonic acid derivatives of the formula (VIII)

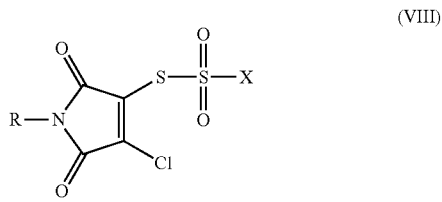

The thiosulphonic acid derivatives of the general formula (VIII) and the polysulphides of the general formula (IX) are new and are likewise provided by the present invention.

In the thiosulphonic acid derivatives of the general formula (VIII), R stands for the definitions of $R^1$ and $R^2$, indicated above, and X stands for chlorine or hydroxyl.

In the polysulphides of the general formula (IX), $R^1$ and $R^2$ stand for the definitions indicated above, and n stands for 0, 1 or 2.

Compounds of the general formula (VIII) are obtained, alongside other products, when the reaction mixture, following the reaction of the compounds of the general formula (VI) with thionyl chloride, is concentrated.

Compounds of the general formula (IX) are obtained, alongside other products, when the reaction mixture, following the reaction of the compounds of the general formula (VI) with thionyl chloride, is concentrated, dissolved in an inert, water-immiscible solvent such as methylene chloride, for example, and extracted by shaking with water at room temperature. Following removal of the organic phase, drying and concentrating, a mixture is obtained which in addition to dithiine-tetracarboximides of the formula (I) contains primarily compounds of the general formula (IX).

The process of the invention for preparing the dithiine-tetracarboximides of the formula (I) can be illustrated by the following scheme:

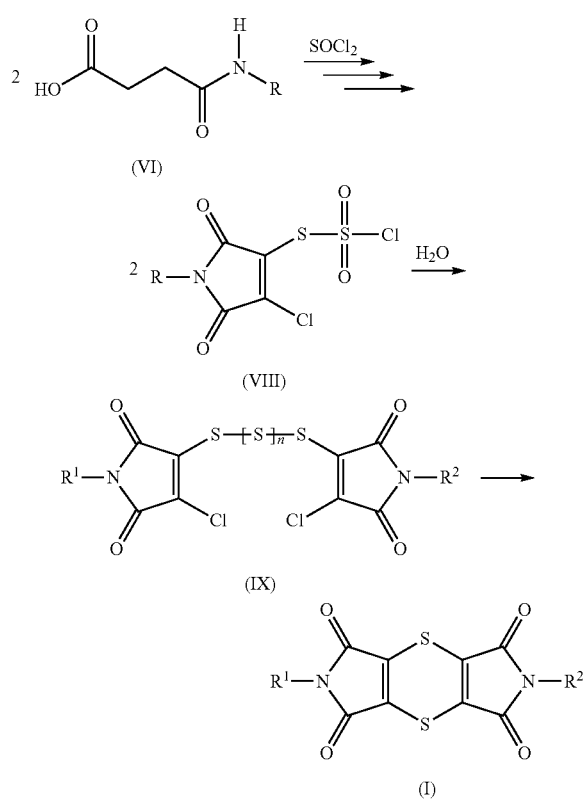

(VI)

(VIII)

(IX)

(I)

R = R¹ or R²

A general definition of the succinic monoamides used as starting materials when carrying out the process of the invention is provided by the formula (VI). R stands for the definitions of $R^1$ or $R^2$.

is $R^1$ and $R^2$ preferably are identical or different and preferably are hydrogen, or are $C_1$-$C_6$-alkyl which is optionally substituted one or more times by fluorine, chlorine, bromine, —$OR^3$ and/or —$COR^4$, or are $C_3$-$C_7$-cycloalkyl which is optionally substituted one or more times by chlorine, methyl or trifluoromethyl, or are phenyl or phenyl-($C_1$-$C_4$-alkyl) each of which is optionally substituted one or more times by fluorine, chlorine, bromine, methyl, trifluoromethyl, —$COR^4$ and/or sulphonylamino.

$R^1$ and $R^2$ more preferably are identical or different and more preferably are hydrogen, or are $C_1$-$C_4$-alkyl which is optionally substituted one or more times by fluorine, chlorine, hydroxyl, methoxy, ethoxy, methylcarbonyloxy and/or carboxyl, or are $C_3$-$C_7$-cycloalkyl which is optionally substituted one or more times by chlorine, methyl or trifluoromethyl, or are phenyl, benzyl, 1-phenethyl, 2-phenethyl or 2-methyl-2-phenethyl each of which is optionally substituted one to three times by fluorine, chlorine, bromine, methyl, trifluoromethyl, —$COR^4$ and/or sulphonylamino.

$R^1$ and $R^2$ very preferably are identical or different and very preferably are hydrogen, methyl, ethyl, n-propyl, isopropyl, 2,2-difluoroethyl or 2,2,2-trifluoroethyl or are cyclopropyl or cyclohexyl each of which is optionally substituted by chlorine, methyl or trifluoromethyl.

$R^1$ and $R^2$ more particularly preferably are simultaneously methyl.

$R^3$ preferably is hydrogen, methyl, ethyl, methylcarbonyl or ethylcarbonyl or is phenyl which is optionally substituted one or more times by fluorine, chlorine, methyl, ethyl, n-propyl, isopropyl or trifluoromethyl.

$R^3$ more preferably is hydrogen, methyl, methylcarbonyl or phenyl, $R^4$ preferably is hydroxyl, methyl, ethyl, methoxy or ethoxy.

$R^4$ more preferably is hydroxyl or methoxy.

As starting material it is particularly preferred to use N-methylsuccinamide, giving as the end product the compound (I-1) 2,6-dimethyl-1H,5H-[1,4]dithiino[2,3-c:5,6-c']dipyrrole-1,3,5,7(2H,6H)-tetrone.

If N-tert-butylsuccinamide is used as starting material, the end product obtained is the compound (I-2) 2,6-di-tert-butyl-1H,5H-[1,4]dithiino[2,3-c:5,6-c']dipyrrole-1,3,5,7(2H,6H)-tetrone.

If N-cyclohexylsuccinamide is used as starting material, the end product obtained is the compound (I-3) 2,6-dicyclohexyl-1H,5H-[1,4]dithiino[2,3-c:5,6-c']dipyrrole-1,3,5,7(2H,1H)-tetrone.

If N-propylsuccinamide is used as starting material, the end product obtained is the compound (I-4) 2,6-dipropyl-1H,5H-[1,4]dithiino[2,3-c:5,6-c']dipyrrole-1,3,5,7(2H,6H)-tetrone.

Intermediates obtained with particular preference are (VIII-1) S-(4-chloro-1-methyl-2,5-dioxo-2,5-dihydro-1H-pyrrol-3-yl)chlorothiosulphate (R=Me, X=Cl), (IX-1) 3,3'-trisulphane-1,3-diylbis(4-chloro-1-methyl-1H-pyrrole-2,5-dione) ($R^1$=$R^2$=Me, n=1)

(IX-2) 3,3'-disulphanediylbis(4-chloro-1-methyl-1H-pyrrole-2,5-dione) ($R^1$=$R^2$=Me, n=0)

(IX-3) 3,3'-disulphanediylbis(1-tert-butyl-4-chloro-1H-pyrrole-2,5-dione) ($R^1$=$R^2$=t-Bu, n=0)

(IX-4) 3,3'-trisulphane-1,3-diylbis(1-tert-butyl-4-chloro-1H-pyrrole-2,5-dione) ($R^1$=$R^2$=t-Bu, n=1)

(IX-5) 3,3'-trisulphane-1,3-diylbis(4-chloro-1-cyclohexyl-1H-pyrrole-2,5-dione) ($R^1$=$R^2$=cyclohexyl, n=1)

The amount of thionyl chloride in the first step of the process of the invention is between 2 and 100 mol per mole of succinic monoamide of the formula (VI). It is preferred to use between 4 and 50 mol, more preferably amounts of between 10 and 40 mol, per mole of succinic monoamide of the formula (VI).

The reaction temperature in the first step of the process of the invention can be varied within wide limits and is between 0° C. and 150° C. In order to obtain satisfactory space-time yields, it is preferred to operate at temperatures between 20° C. and 120° C., more preferably between 30° C. and 100° C.

The reaction time in the first step of the process of the invention is between 10 minutes and 24 hours. It is preferred to operate for between 30 minutes and 6 hours, more preferably between 1 and 4 hours.

The first step of the process of the invention can be carried out optionally in the presence of a diluent which as far as possible is inert under the reaction conditions. Such diluents include, by way of example, aliphatic hydrocarbons such as pentane, hexane, heptane, cyclohexane, methylcyclohexane, chlorinated hydrocarbons such as methylene chloride, chloroform, 1,2-dichloroethane, aromatic hydrocarbons such as toluene, xylene, mesitylene, chlorinated aromatic hydrocarbons such as chlorobenzene, dichlorobenzene, ethers such as diethyl ether, methyl tert-butyl ether, tetrahydrofuran, dioxane, nitriles such as acetonitrile, butyronitrile, esters such as methyl acetate and ethyl acetate. It is preferred to operate in methylene chloride, chloroform or 1,2-dichloroethane or without diluent.

The thionyl chloride can be removed in principle by hydrolysis with water. The thionyl chloride is removed preferably by distillation under reduced pressure.

The diluent optionally present is preferably likewise distilled off under reduced pressure.

In the second step of the process of the invention, the residue that is obtained following removal of the excess thionyl chloride and optionally of the diluent is dissolved in a new diluent and, by heating in this solvent, is converted into the dithiine-carboximides of the formula (I). The reaction mixture is preferably stirred during this procedure.

In the second step of the process of the invention, organic solvents or solvent mixtures are used. These solvents are preferably at least partly miscible with water.

Suitable diluents for the second step of the process of the invention include, specifically, water, dimethyl sulphoxide, sulpholane, alcohols such as, for example, methanol, ethanol, propanol, isopropanol, 1-butanol, 2-butanol, isobutanol, tertiary-butanol, 1-pentanol, cyclopentanol, cyclohexanol, ethylene glycol, ethylene glycol monomethyl ether, hydrocarbons such as hexane, heptane, cyclohexane, methylcyclohexane, toluene, xylenes, mesitylene, chlorobenzene, dichlorobenzene, nitrobenzene, esters such as methyl acetate, ethyl acetate, amides such as formamide, N,N-ditmethylformamide; N,N-dimethylacetamide, N-methylpyrrolidone, ethers such as methyl tert-butyl ether, tetrahydrofuran, 1,4-dioxane, nitriles such as acetonitrile, propionitrile, butyronitrile, benzonitrile, ketones such as acetone, methyl ethyl ketone, methyl isobutyl ketone, pinacolone, carboxylic acids such as formic acid, acetic acid, propionic acid, or mixtures of these diluents.

Preference is given to using water, dimethyl sulphoxide, methanol, ethanol, propanol, isopropanol, 1-butanol, 2-butanol, isobutanol, tertiary-butanol, 1-pentanol, cyclohexanol, ethylene glycol, methyl acetate, N,N-dimethylformamide; N,N-dimethylacetamide, tetrahydrofuran, 1,4-dioxane, acetonitrile, acetone, methyl ethyl ketone, methyl isobutyl ketone, acetic acid or mixtures of these diluents.

Very particular preference is given to using mixtures of water and methanol, ethanol, propanol, isopropanol, 1-butanol, 2-butanol, isobutanol, 1-pentanol, methyl acetate, tetrahydrofuran, 1,4-dioxane, acetonitrile, acetone, acetic acid.

The mixing ratio of water to organic solvent here may be varied within wide limits of, for example, 9:1 to 1:9.

The reaction temperature in the second step of the process of the invention can be varied within wide limits and is between 0° C. and 200° C. It is preferred to operate at temperatures between 20° C. and 150° C., more preferably between 30° C. and 130° C.

The reaction time in the second step of the process of the invention is between 5 minutes and 24 hours. It is preferred to operate for between 30 minutes and 12 hours, more preferably between 1 and 6 hours.

The process of the invention is illustrated by, but not confined to, the following examples.

EXAMPLE 1

N-Methylsuccinamide [5.24 g; 40 mmol] is introduced and at 15° C. 142.8 g [1200 mmol] of thionyl chloride are added dropwise. The mixture is then heated to 80° C. and stirred at this temperature for 1 hour. The reaction mixture is concentrated on a rotary evaporator. This gives 9.9 g of a thick brown oil which according to HPLC and LC/MS analysis contains 19.2 area % of compound (VIII-1), 36.1 area % of compound (I-1) and 19.1 area % of compound (IX-1).

Compound (VIII-1) (R=Me):
LC/MS (ESI neg.): m/z=256 ([M-H$^+$], $^{35}$Cl; 65%), 176 ([M-H$^+$]-80, $^{35}$Cl, 100%).

$^{13}$C-NMR (CDCl$_3$): δ=25.1 (N—CH$_3$), 135.5, 138.1 (=C—Cl, =C—S), 162.9, 164.9 (—CO—CS, —CO—C—Cl) ppm.

EXAMPLE 2

A solution of 10.5 g [80 mmol] of N-methylsuccinamide in 100 ml of methylene chloride is admixed dropwise at 15° C. with 285.6 g [2400 mmol] of thionyl chloride. The mixture is allowed to reach room temperature, and then is heated to 40° C. and stirred at that temperature for 16 hours. It is cooled to room temperature and the reaction mixture is stirred into 800 g of ice-water. After overnight standing at room temperature, the organic phase is isolated, the aqueous phase is extracted with methylene chloride, and the combined organic phases are dried and then concentrated on a rotary evaporator. This gives 11.8 g of a thick brown oil which according to HPLC and LC/MS analysis contains 25.7 area % of compound (I-1), 22.9 area % of compound (IX-2) and 37.7 area % of compound (IX-1).

Compound (IX-2):
LC/MS (ESI pos.): m/z=353 (MH$^+$, 2x$^{35}$Cl).
$^{13}$C-NMR (CD$_3$CN): δ=25.4 (N—CH$_3$), 136.1, 139.4 (=C—S, =C—Cl), 164.4, 166.2 (—CO—C—Cl, —CO—C—S) ppm.

Compound (IX-1):
LC/MS (ESI pos.): m/z=385 (MH$^+$, 2x$^{35}$Cl).
$^{13}$C-NMR (CDCl$_3$): δ=25.3 (N—CH$_3$), 136.1, 140.0 (=C—S, =C—Cl), 164.3, 166.2 (—CO—C—Cl, —CO—C—S) ppm.

EXAMPLE 3

Of the product mixture from Example 2, 0.2 g is dissolved in 10 ml of methanol and heated at 60° C. for 4 hours. Following removal of the solvent, the composition is as follows: 61.1 area % of compound (I-1), 9.7 area % of compound (IX-2) and 2.5 area % of compound (IX-1).

EXAMPLE 4

Of the product mixture from Example 2, 0.2 g is dissolved in 10 ml of methanol/water (1:1) and heated at 60° C. for 4 hours. Following removal of the solvent, the composition is as follows: 90.1 area % of compound (I-1), <0.1 area % of compound (IX-2) and <0.1 area % of compound (IX-1).

EXAMPLE 5

Of the product mixture from Example 2, 0.2 g is dissolved in 10 ml of 1,4-dioxane/water (1:1) and heated at 60° C. for 4 hours. Following removal of the solvent, the composition is as follows: 84.6 area % of compound (1-<0.1 area % of compound (IX-2) and <0.1 area % of compound (IX-1).

EXAMPLE 6

Of the product mixture from Example 2, 0.2 g is dissolved in 10 ml of DMF and heated at 60° C. for 4 hours. Following removal of the solvent, the composition is as follows: 71.1 area % of compound (I-1), <0.1 area % of compound (IX-2) and <0.1 area % of compound (IX-1).

EXAMPLE 7

Of the product mixture from Example 2, 0.2 g is dissolved in 10 ml of acetonitrile/water (1:1) and heated at 60° C. for 4 hours. Following removal of the solvent, the composition is as follows: 85.4 area % of compound (I-1), <0.1 area % of compound (IX-2) and <0.1 area % of compound (IX-1).

EXAMPLE 8

Of the product mixture from Example 2, 0.2 g is dissolved in 10 ml of acetone/water (1:1) and heated at 60° C. for 4 hours. Following removal of the solvent, the composition is as follows: 85.1 area % of compound (I-1), <0.1 area % of compound (IX-2) and <0.1 area % of compound (IX-1).

EXAMPLE 9

Of the product mixture from Example 2, 0.2 g is dissolved in 10 ml of methyl acetate/water (1:1) and heated at 60° C. for 4 hours. Following removal of the solvent, the composition is as follows 89 area % of compound (I-1), <0.1 area % of compound (IX-2) and <0.1 area % of compound (IX-1).

EXAMPLE 10

A solution of 5.24 g [40 mmol] of N-methylsuccinamide in 50 ml of methylene chloride is admixed dropwise at 15° C. with 142.8 g [1200 mmol] of thionyl chloride. The mixture is allowed to reach room temperature, and then is heated to 40° C. and stirred at that temperature for 1 hour. The mixture is cooled to room temperature and concentrated on a rotary evaporator. This gives 12 g of a thick brown oil, which is dissolved in 100 ml of ethanol. This solution is heated at 60° C. for 4 hours and then cooled to room temperature. The dark-green solid precipitated is isolated by filtration with suction, washed with EtOH and water and dried. This gives 2.92 g of solid which according to HPLC analysis is composed to an extent of 99.1 area % of the compound (I-1), corresponding to a yield of 51.3% of theory.

EXAMPLE 11

A solution of 5.24 g [40 mmol] of N-methylsuccinamide in 50 ml of 1,4-dioxane is admixed dropwise at 15° C. with 142.8 g [1200 mmol] of thionyl chloride. The mixture is allowed to reach room temperature, and then is heated to 80° C. and stirred at that temperature for 1 hour. The mixture is cooled to room temperature and concentrated on a rotary evaporator. This gives 10.9 g of a thick brown oil, which is dissolved in 100 ml of ethanol. This solution is heated at 60° C. for 4 hours and then cooled to room temperature. The dark-green solid precipitated is isolated by filtration with suction, washed with EtOH and water and dried. This gives 2.66 g of solid which according to HPLC analysis is composed to an extent of 99.4 area % of the compound (I-1), corresponding to a yield of 46.8% of theory.

EXAMPLE 12

N-Methylsuccinamide [5.24 g; 40 mmol] is introduced and, at 15° C., 142.8° g [1200 mmol] of thionyl chloride are added dropwise. The mixture is then heated to 80° C. and stirred at this temperature for 1 hour. The reaction mixture is concentrated on a rotary evaporator. The residue (dark-brown, thick oil) is admixed with 100 ml of methanol/water (1:1) and heated at 60° C. for 4 hours. Thereafter it is allowed to cool to room temperature and the precipitated solid is isolated by filtration with suction and washed with water and methanol. Drying produces 4.30 g of dark-green solid, which according to HPLC analysis is composed to an extent of 94.7 area % of the compound (I-1), corresponding to a yield of 72.1% of theory.

EXAMPLE 13

N-Methylsuccinamide [5.24 g; 40 mmol] is introduced and, at 15° C., 47.6 g [400 mmol] of thionyl chloride are added dropwise. The mixture is then heated to 80° C. and stirred at this temperature for 1 hour. The reaction mixture is concentrated on a rotary evaporator. The residue (dark-brown, thick oil) is admixed with 100 ml of methanol/water (1:1) and heated at 60° C. for 4 hours. Thereafter it is allowed to cool to room temperature and the precipitated solid is isolated by filtration with suction and washed with water and methanol. Drying produces 4.05 g of dark-green solid, which according to HPLC analysis is composed to an extent of 97.8 area % of the compound (I-1), corresponding to a yield of 70.2% of theory.

COMPARATIVE EXAMPLE 1

A solution of 5.24 g [40 mmol] of N-methylsuccinamide in 50 ml of 1,4-dioxane is admixed dropwise at 15° C. with 142.8 g [1200 mmol] of thionyl chloride. The mixture is allowed to come to room temperature and is stirred at room temperature of 16 hours. The reaction mixture is stirred into approximately 400 g of ice-water. Approximately 100 ml of ethyl acetate are added and the green solid precipitated is isolated by filtration with suction, washed with water and ethyl acetate and dried. This gives 1.00 g of solid with a purity of 80.8 area %, corresponding to a yield of 14.3% of theory. The organic phase of the filtrate is separated off and washed with water. As a result, further solid is precipitated at the phase interface: 0.40 g, 99.1% purity (7.2% of theory). The filtrate of the organic phase is concentrated and the residue is stirred together with methyl tert-butyl ether (MTBE). The resulting solid is isolated by filtration with suction and dried: 0.70 g, 51.0% purity (6.3% of theory). The collected aqueous phases are left to stand at room temperature for 2 days; after this time, further solid has precipitated, and is likewise isolated: 0.50 g, 99.1% purity (8.8% of theory). Overall, therefore, the yield obtained is 36.5% of theory of compound (I-1).

COMPARATIVE EXAMPLE 2

A solution of 5.24 g [40 mmol] of N-methylsuccinamide in 50 ml of 1,4-dioxane is admixed dropwise at 15° C. with 142.8 g [1200 mmol] of thionyl chloride. The mixture is allowed to come to room temperature, and then is heated to 80° C. and stirred at this temperature for 1 hour. It is cooled to room temperature, stirred into approximately 400 g of ice-water and left to stand overnight, and the green solid precipitated is isolated by filtration with suction, washed with water and ethyl acetate and dried. This gives 3.75 g of solid with a purity of only 76.5 area % (50.8% of theory).

EXAMPLE 14

N-tert-butylsuccinamide [6.93 g; 40 mmol] is introduced and, at 15° C., 142.8 g [1200 mmol] of thionyl chloride are added dropwise. The mixture is then heated to 80° C. and stirred at this temperature for 1 hour. The reaction mixture is concentrated on a rotary evaporator. The resulting thick brown oil is dissolved in methylene chloride and washed with saturated aqueous NaCl solution. The organic phase is dried over sodium sulphate and concentrated. This gives 7.65 g of brown residue which according to HPLC and LC/MS contains 14.3 area % of compound (IX-3) and 9.7 area % of compound (IX-4).

Compound (IX-3):
LC/MS (ESI pos.): m/z=437 ([MH$^+$], 2×$^{35}$Cl; 60%), 454 ([MH$^+$]+NH$_3$, 2×$^{35}$Cl, 100%).

Compound (IX-4):
LC/MS (ESI pos.): m/z=469 ([MH$^+$], 2×$^{35}$Cl; 20%), 486 ([MH$^+$]+NH$_3$, 2×$^{35}$Cl, 100%).

EXAMPLE 15

N-tert-butylsuccinamide [6.93 g; 40 mmol] is introduced and, at 15° C., 142.8 g [1200 mmol] of thionyl chloride are added dropwise. The mixture is then heated to 50° C. and stirred at this temperature for 4 hours. The reaction mixture is concentrated on a rotary evaporator. The resulting thick brown oil is taken up in 100 ml of EtOH/H$_2$O (1:1) and heated at 60° C. for 4 hours. Thereafter, the system is cooled to room temperature and the solid is isolated by filtration with suction, washed with water and EtOH and dried. This gives 5.00 g of brown solid which according to HPLC contains 99.6 area % of compound (I-3).

EXAMPLE 16

N-cyclohexylsuccinamide [8 g; 40 mmol] is introduced and, at 15° C., 142.8 g [1200 mmol] of thionyl chloride are added dropwise. The mixture is then heated to 80° C. and stirred at this temperature for 1 hour. The reaction mixture is concentrated on a rotary evaporator. The resulting thick brown oil is dissolved in methylene chloride and washed with saturated aqueous NaCl solution. The organic phase is dried over sodium sulphate and concentrated. This gives 10.8 g of brown residue which according to HPLC and LC/MS contains 19 area % of compound (IX-5).

Compound (IX-5):
LC/MS (ESI pos.): m/z=521 ([MH$^+$], 2×$^{35}$Cl; 70%), 538 ([MH$^+$]+NH$_3$, 2×$^{35}$Cl, 100%).

EXAMPLE 17

N-cyclohexylsuccinamide [8 g; 40 mmol] is introduced and, at 15° C., 142.8 g [1200 mmol] of thionyl chloride are added dropwise. The mixture is then heated to 50° C. and stirred at this temperature for 4 hours. The reaction mixture is concentrated on a rotary evaporator. The resulting thick brown oil is taken up in 100 ml of EtOH/H$_2$O (1:1) and heated at 60° C. for 4 hours. Thereafter, the system is cooled to room temperature and the solid is isolated by filtration with suction, washed with water and EtOH and dried. This gives 2.86 g of brown solid which according to HPLC contains 92.1 area % of compound (I-3).

EXAMPLE 18

N-propylsuccinamide [6.37 g; 40 mmol] is introduced and, at 15° C., 142.8 g [1200 mmol] of thionyl chloride are added dropwise. The mixture is then heated to 50° C. and stirred at this temperature for 4 hours. The reaction mixture is concentrated on a rotary evaporator. The resulting thick brown oil is taken up in 100 ml of EtOH/H$_2$O (1:1) and heated at 60° C. for 4 hours. Thereafter, the system is cooled to room temperature and the solid is isolated by filtration with suction, washed with water and EtOH and dried. This gives 2.15 g of green solid which according to HPLC contains 99.4 area % of compound (I-4).

General Information:

HPLC conditions: Zorbax Eclipse Plus C18 4.6*50 mm 1.8 μm, eluent A: 0.1% H$_3$PO$_4$, eluent B: acetonitrile, gradient: 90/10, 20%/min, 5/95 (1.75), flow rate: 2 ml/min, 55° C.

The invention claimed is:

1. A process for preparing a compound of formula (I)

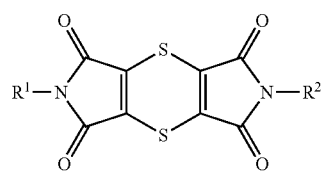

in which
R$^1$ and R$^2$ are identical or different and are hydrogen; C$_1$-C$_8$-alkyl which is optionally substituted with one or more halogen, —OR$^3$, or —COR$^4$; C$_3$-C$_7$-cycloalkyl which is optionally substituted with one or more halogen, C$_1$-C$_4$-alkyl, or C$_1$-C$_4$-haloalkyl; or aryl or aryl-(C$_1$-C$_4$-alkyl) each of which is optionally substituted with one or more halogen, C$_1$-C$_4$-alkyl, C$_1$-C$_4$-haloalkyl, —COR$^4$, or sulphonylamino, R$^3$ is hydrogen, C$_1$-C$_4$-alkyl, C$_1$-C$_4$-alkylcarbonyl, or aryl, wherein the aryl is optionally substituted with one or more halogen, C$_1$-C$_4$-alkyl, or C$_1$-C$_4$-haloalkyl, R$^4$ is hydroxyl, C$_1$-C$_4$-alkyl, or C$_1$-C$_4$-alkoxy, comprising:

(1) reacting succinic monoamides of formula (VI)

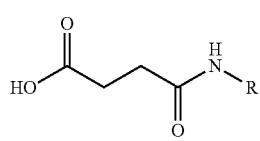

in which R is R$^1$ or R$^2$ with an excess of thionyl chloride, optionally in the presence of a diluent;

(2) removing thionyl chloride to form a product mixture; and (3) adding an organic solvent to the product mixture and after a reaction time of between 5 minutes and 24 hours converting, into a compound of formula (I).

2. The process according to claim 1, wherein in (1), between 2 and 100 moles of thionyl chloride are used per mole of succinic monoamide of formula (VI).

3. The process according to claim 1, wherein (1) is carried out without diluent.

4. The process according to claim 1, wherein the organic solvent in (3) is at least partly miscible with water.

5. The process according to claim 1, wherein the organic solvent in (3) is water, dimethyl sulphoxide, sulpholane, an alcohol, a hydrocarbon, an ester, an ether, a nitrile, a carboxylic acid, or mixtures thereof.

6. The process according to claim 1, wherein (3) is carried out with heating.

7. A process for preparing a mixture comprising:
(1) a compound of formula (IX),

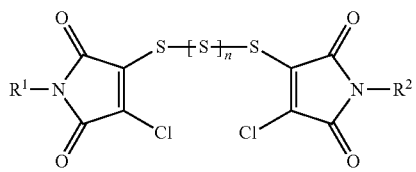

in which
R¹ and R² are identical or different and are hydrogen; $C_1$-$C_8$-alkyl which is optionally substituted with one or more halogen, —$OR^3$, or —$COR^4$; $C_3$-$C_7$-cycloalkyl which is optionally substituted with one or more halogen, $C_1$-$C_4$-alkyl, or $C_1$-$C_4$-haloalkyl; or aryl or aryl-($C_1$-$C_4$-alkyl) each of which is optionally substituted with one or more halogen, $C_1$-$C_4$-alkyl, $C_1$-$C_4$-haloalkyl, —$COR^4$, or sulphonylamino,
$R^3$ is hydrogen, $C_1$-$C_4$-alkyl, $C_1$-$C_4$-alkylcarbonyl, or is aryl, wherein the aryl is optionally substituted with one or more halogen, $C_1$-$C_4$-alkyl, or $C_1$-$C_4$-haloalkyl,
$R^4$ is hydroxyl, $C_1$-$C_4$-alkyl, or $C_1$-$C_4$-alkoxy,
n is 0, 1, or 2, and
(2) a compound of formula (VIII)

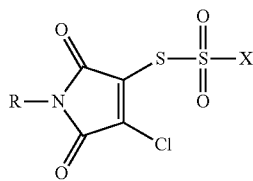

in which R is $R^1$ or $R^2$ and X is chlorine or hydroxyl, comprising reacting a compound of formula (VI)

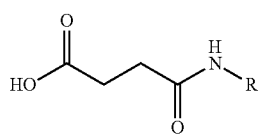

in which R is $R^1$ or $R^2$ with an excess of thionyl chloride, optionally in the presence of a diluent.

8. A compound of formula (IX),

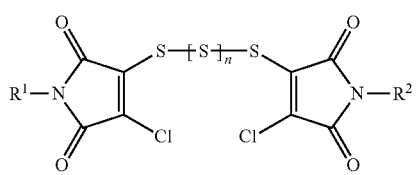

in which
R¹ and R² are identical or different and are hydrogen; $C_1$-$C_8$-alkyl which is optionally substituted with one or more halogen, —$OR^3$, or —$COR^4$; $C_3$-$C_7$-cycloalkyl which is optionally substituted with one or more halogen, $C_1$-$C_4$-alkyl, or $C_1$-$C_4$-haloalkyl; or aryl or aryl-($C_1$-$C_4$-alkyl) each of which is optionally substituted with one or more halogen, $C_1$-$C_4$-alkyl, $C_1$-$C_4$-haloalkyl, —$COR^4$, or sulphonylamino,
$R^3$ is hydrogen, $C_1$-$C_4$-alkyl, $C_1$-$C_4$-alkylcarbonyl, or aryl, wherein the aryl is optionally substituted with one or more halogen, $C_1$-$C_4$-alkyl, or $C_1$-$C_4$-haloalkyl,
$R^4$ is hydroxyl, $C_1$-$C_4$-alkyl, or $C_1$-$C_4$-alkoxy,
n is 0, 1, or 2.

9. A compound of formula (VIII)

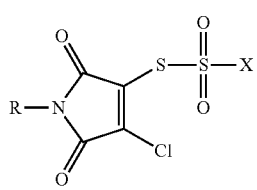

in which
R is hydrogen; $C_1$-$C_8$-alkyl which is optionally substituted with one or more halogen, —$OR^3$, or —$COR^4$; $C_3$-$C_7$-cycloalkyl which is optionally substituted with one or more halogen, $C_1$-$C_4$-alkyl, or $C_1$-$C_4$-haloalkyl; or aryl or aryl-($C_1$-$C_4$-alkyl) each of which is optionally substituted with one or more halogen, $C_1$-$C_4$-alkyl, $C_1$-$C_4$-haloalkyl, —$COR^4$, or sulphonylamino,
$R^3$ is hydrogen, $C_1$-$C_4$-alkyl, $C_1$-$C_4$-alkylcarbonyl, or aryl, wherein the aryl is optionally substituted with one or more halogen, $C_1$-$C_4$-alkyl, or $C_1$-$C_4$-haloalkyl,
$R^4$ is hydroxyl, $C_1$-$C_4$-alkyl, or $C_1$-$C_4$-alkoxy;
X is chlorine or hydroxyl.

10. The process of claim 1, wherein in (1), between 4 and 50 moles of thionyl chloride are used per mole of the succinic monoamide of formula (VI).

11. The process of claim 1, wherein in (1), between 10 and 40 moles of thionyl chloride are used per mole of the succinic monoamide of formula (VI).

12. The process of claim 1, wherein the organic solvent in (3) is selected from water, dimethyl sulphoxide, methanol, ethanol, propanol, isopropanol, 1-butanol, 2-butanol, isobutanol, tertiary-butanol, 1-pentanol, cyclopentanol, cyclohexanol, ethylene glycol, ethylene glycol monomethyl ether, hexane, heptane, cyclohexane, methylcyclohexane, toluene, xylenes, mesitylene, chlorobenzene, dichlorobenzene, nitrobenzene, methyl acetate, ethyl acetate, formamide, N,N-dimethylformamide, dimethylacetamide, N-methylpyrrolidone, methyl tert-butyl ether, tetrahydrofuran, 1,4-dioxane, acetonitrile, propionitrile, butyronitrile, benzonitrile, acetone, methyl ethyl ketone, methyl isobutyl ketone, pinacolone, formic acid, acetic acid, propionic acid, or mixtures thereof.

13. The process of claim 1, wherein the organic solvent in (3) is selected from water, methanol, ethanol, propanol, isopropanol, 1-butanol, 2-butanol, isobutanol, 1-pentanol, methyl acetate, tetrahydrofuran, 1,4-dioxane, acetonitrile, acetone, acetic acid, or mixtures thereof.

14. The process of claim 1, wherein the succinic monoamide is N-methylsuccamide, N-butylsuccinamide, N-cyclohexylsuccinamide, or N-propylsuccinamide.

15. The process of claim 1, wherein the compound of formula (I) is selected from:
2,6-dimethyl-1H,5H-[1,4]dithiino[2,3-c:5,6-c']dipyrrole-1,3,5,7(2H,6H)-tetrone;

2,6-di-tert-butyl-1H,5H-[1,4]dithiino[2,3-c:5,6-c']dipyrrole-1,3,5,7(2H,6H)-tetrone;

2,6-dicyclohexyl-1H,5H-[1,4]dithiino[2,3-c:5,6-c']dipyrrole-1,3,5,7(2H,6H)-tetrone; or 2,6-dipropyl-1H,5H-[1,4]dithiino[2,3-c:5,6-c']dipyrrole-1,3,5,7(2H,6H)-tetrone.

16. The compound of claim 8, selected from:

3,3'-trisulphane-1,3-diylbis(4-chloro-1-methyl-1H-pyrrole-2,5-dione);

3,3'-disulphanediylbis(4-chloro-1-methyl-1H-pyrrole-2,5-dione);

3,3'-disulphanediylbis(1-tert-butyl-4-chloro-1H-pyrrole-2,5-dione);

3,3'-trisulphane-1,3-diylbis(1-tert-butyl-4-chloro-1H-pyrrole-2,5-dione); or 3,3'-trisulphane-1,3-diylbis(4-chloro-1-cyclohexyl-1H-pyrrole-2,5-dione).

17. The process of claim 1, wherein the thionyl chloride is removed by distillation.

18. The process of claim 1, wherein (3) is carried out at a temperature between 30° C. and 130° C.

19. The process of claim 1, wherein in (3) the reaction time is between 30 minutes and 12 hours.

* * * * *